United States Patent
Lin et al.

(10) Patent No.: US 7,097,793 B2
(45) Date of Patent: *Aug. 29, 2006

(54) METHOD FOR MAKING A POROUS CALCIUM PHOSPHATE ARTICLE

(75) Inventors: Jiin-Huey Chern Lin, Winnetka, IL (US); Chien-Ping Ju, Carbondale, IL (US); Yin-Chun Tien, Kaohsiung (TW); Chih-Hung Tsai, Taichung (TW); Chao-Chin Ning, Kaohsiung (TW); Chung-Po Chao, Bade (TW)

(73) Assignee: Calcitec, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/071,803

(22) Filed: Mar. 3, 2005

(65) Prior Publication Data

US 2005/0184418 A1 Aug. 25, 2005

Related U.S. Application Data

(63) Continuation of application No. 10/780,728, filed on Feb. 19, 2004.

(51) Int. Cl.
*A61F 2/28* (2006.01)
*B29C 39/02* (2006.01)

(52) U.S. Cl. .................... 264/42; 264/49; 264/333

(58) Field of Classification Search ................ 264/42, 264/49, 333, 86, 87, 250, 251
See application file for complete search history.

(56) References Cited

U.S. PATENT DOCUMENTS

| | | | |
|---|---|---|---|
| 3,679,360 A | 7/1972 | Rubin et al. | |
| 4,371,484 A | 2/1983 | Inukai et al. | |
| 4,481,175 A | 11/1984 | Iino et al. | |
| 4,518,430 A | 5/1985 | Brown et al. | |
| 4,553,272 A | 11/1985 | Mears | |
| 4,612,053 A | 9/1986 | Brown et al. | |
| 4,623,553 A | 11/1986 | Ries et al. | |
| RE33,161 E | * 2/1990 | Brown et al. ............... | 423/308 |
| RE33,221 E | 5/1990 | Brown et al. | |
| 4,959,104 A | 9/1990 | Iino et al. | |
| 5,017,518 A | 5/1991 | Hirayama et al. | |
| 5,053,212 A | 10/1991 | Constantz et al. | |
| 5,092,888 A | 3/1992 | Iwamoto et al. | |
| 5,149,368 A | 9/1992 | Liu et al. | |
| 5,152,791 A | 10/1992 | Hakamatsuka et al. | |
| 5,164,187 A | 11/1992 | Constantz et al. | |
| 5,180,426 A | 1/1993 | Sumita | |
| 5,262,166 A | 11/1993 | Liu et al. | |
| 5,336,264 A | 8/1994 | Constanz et al. | |
| 5,338,356 A | 8/1994 | Hirano et al. | |
| 5,342,441 A | 8/1994 | Mandai et al. | |
| 5,409,982 A | 4/1995 | Imura et al. | |
| 5,476,647 A | 12/1995 | Chow et al. | |
| 5,492,768 A | 2/1996 | Okimatsu et al. | |
| 5,496,399 A | 3/1996 | Ison et al. | |
| 5,503,164 A | 4/1996 | Friedman | |
| 5,522,893 A | 6/1996 | Chow et al. | |
| 5,525,148 A | 6/1996 | Chow et al. | |
| 5,536,575 A | 7/1996 | Imura et al. | |
| 5,542,973 A | 8/1996 | Chow et al. | |
| 5,545,254 A | 8/1996 | Chow et al. | |
| 5,550,172 A | 8/1996 | Regula et al. | |
| 5,569,490 A | 10/1996 | Imura et al. | |
| 5,605,713 A | 2/1997 | Boltong | |
| 5,607,685 A | 3/1997 | Cimbollek et al. | |
| 5,652,016 A | 7/1997 | Imura et al. | |
| 5,683,461 A | 11/1997 | Lee et al. | |
| 5,683,496 A | 11/1997 | Ison et al. | |
| 5,695,729 A | 12/1997 | Chow et al. | |
| 5,697,981 A | 12/1997 | Ison et al. | |
| 5,702,449 A | 12/1997 | McKay | |
| 5,766,669 A | 6/1998 | Pugh et al. | |
| 5,782,971 A | 7/1998 | Constantz et al. | |
| 5,814,681 A | 9/1998 | Hino et al. | |
| 5,820,632 A | 10/1998 | Constantz et al. | |
| 5,846,312 A | 12/1998 | Ison et al. | |
| 5,891,448 A | 4/1999 | Chow et al. | |
| 5,899,939 A | 5/1999 | Boyce et al. | |
| 5,954,867 A | 9/1999 | Chow et al. | |

(Continued)

FOREIGN PATENT DOCUMENTS

EP 0267624 5/1988

(Continued)

OTHER PUBLICATIONS

PCT/US04/11637 International Search Report/Written Opinion, Oct. 2004, Examiner Koslow.

(Continued)

*Primary Examiner*—Mary Lynn Theisen
(74) *Attorney, Agent, or Firm*—Meyertons, Hood, Kivlin, Kowert & Goetzel, P.C.; Eric B. Meyertons

(57) ABSTRACT

The present invention discloses a method for making a porous calcium phosphate article including i) preparing a shaped article from a paste containing a calcium phosphate cement, a pore-forming powder and a setting liquid; ii) immersing the shaped article in an immersing liquid for a period of time so that the pore-forming powder is dissolved in the immersing liquid, creating pores in said shaped article; and iii) removing the resulting porous shaped article from the immersing liquid, wherein the resulting porous shaped article has an improved compressive strength. The porous shaped calcium phosphate article of the present invention may be used as a tissue-engineered scaffold, medical implant or a reinforcing constituent of a composite.

22 Claims, No Drawings

U.S. PATENT DOCUMENTS

| | | | |
|---|---|---|---|
| 5,958,430 | A | 9/1999 | Campbell et al. |
| 5,964,932 | A | 10/1999 | Ison et al. |
| 5,976,234 | A | 11/1999 | Chow et al. |
| 5,993,535 | A | 11/1999 | Sawamura et al. |
| 5,997,624 | A | 12/1999 | Chow et al. |
| 6,005,162 | A | 12/1999 | Constantz |
| 6,013,591 | A | 1/2000 | Ying et al. |
| 6,013,853 | A | 1/2000 | Athanasiou et al. |
| 6,018,095 | A | 1/2000 | Lerch et al. |
| 6,027,742 | A | 2/2000 | Lee et al. |
| 6,077,989 | A | 6/2000 | Kandel et al. |
| 6,117,456 | A | 9/2000 | Lee et al. |
| 6,118,043 | A | 9/2000 | Nies et al. |
| 6,123,731 | A | 9/2000 | Boyce et al. |
| 6,132,463 | A | 10/2000 | Lee et al. |
| 6,149,688 | A | 11/2000 | Brosnahan et al. |
| 6,162,258 | A | 12/2000 | Scarborough et al. |
| 6,277,149 | B1 | 8/2001 | Boyle et al. |
| 6,294,041 | B1 | 9/2001 | Boyce et al. |
| 6,294,187 | B1 | 9/2001 | Boyce et al. |
| 6,323,146 | B1 | 11/2001 | Pugh et al. |
| 6,325,987 | B1 | 12/2001 | Sapieszko et al. |
| 6,325,992 | B1 | 12/2001 | Chow et al. |
| 6,332,779 | B1 | 12/2001 | Boyce et al. |
| 6,340,648 | B1 | 1/2002 | Imura et al. |
| 6,379,453 | B1 | 4/2002 | Lin et al. |
| 6,440,444 | B1 | 8/2002 | Boyce et al. |
| 6,458,162 | B1 | 10/2002 | Koblish et al. |
| 6,478,825 | B1 | 11/2002 | Winterbottom et al. |
| 6,495,156 | B1 | 12/2002 | Wenz et al. |
| 6,530,955 | B1 | 3/2003 | Boyle et al. |
| 6,547,866 | B1 | 4/2003 | Edwards et al. |
| 6,569,489 | B1 | 5/2003 | Li |
| 6,585,992 | B1 | 7/2003 | Pugh et al. |
| 6,616,742 | B1 | 9/2003 | Lin et al. |
| 6,648,960 | B1 | 11/2003 | Lin et al. |
| 6,670,293 | B1 | 12/2003 | Edwards et al. |
| 6,696,073 | B1 | 2/2004 | Boyce et al. |
| 6,719,989 | B1 | 4/2004 | Matsushima et al. |
| 6,752,831 | B1 | 6/2004 | Sybert et al. |
| 6,793,725 | B1 | 9/2004 | Chow et al. |
| 6,808,561 | B1 | 10/2004 | Genge et al. |
| 6,808,585 | B1 | 10/2004 | Boyce et al. |
| 6,840,995 | B1 | 1/2005 | Lin et al. |
| 6,929,692 | B1 | 8/2005 | Tas |
| 6,953,594 | B1 | 10/2005 | Lee et al. |
| 6,955,716 | B1 | 10/2005 | Xu et al. |
| 6,960,249 | B1 | 11/2005 | Lin et al. |
| 2002/0019635 | A1 | 2/2002 | Wenstrom, Jr. et al. |
| 2002/0073894 | A1 | 6/2002 | Genge et al. |
| 2002/0137812 | A1 | 9/2002 | Chow et al. |
| 2002/0169066 | A1 | 11/2002 | Cassidy et al. |
| 2003/0019396 | A1 | 1/2003 | Edwards et al. |
| 2003/0021824 | A1* | 1/2003 | Lacout et al. ............... 424/423 |
| 2003/0031698 | A1 | 2/2003 | Roeder et al. |
| 2003/0039676 | A1 | 2/2003 | Boyce et al. |
| 2003/0055512 | A1 | 3/2003 | Genin et al. |
| 2003/0074081 | A1 | 4/2003 | Ayers et al. |
| 2003/0078317 | A1 | 4/2003 | Lin et al. |
| 2003/0120351 | A1 | 6/2003 | Tofighi |
| 2003/0121450 | A1 | 7/2003 | Lin et al. |
| 2003/0167093 | A1 | 9/2003 | Xu et al. |
| 2003/0216777 | A1 | 11/2003 | Tien et al. |
| 2004/0003757 | A1 | 1/2004 | Lin et al. |
| 2004/0022825 | A1 | 2/2004 | Lagow |
| 2004/0031420 | A1 | 2/2004 | Lin et al. |
| 2004/0076685 | A1 | 4/2004 | Tas |
| 2004/0137032 | A1 | 7/2004 | Wang |
| 2004/0175320 | A1 | 9/2004 | Lin et al. |
| 2004/0180091 | A1 | 9/2004 | Lin |
| 2004/0185181 | A1 | 9/2004 | Matsumoto |
| 2004/0186481 | A1 | 9/2004 | Lin et al. |
| 2005/0008759 | A1 | 1/2005 | Nie et al. |
| 2005/0076813 | A1 | 4/2005 | Lin et al. |
| 2005/0101964 | A1 | 5/2005 | Lin et al. |
| 2005/0184417 | A1 | 8/2005 | Lin et al. |
| 2005/0186353 | A1 | 8/2005 | Lin et al. |
| 2005/0186354 | A1 | 8/2005 | Lin et al. |
| 2005/0186449 | A1 | 8/2005 | Lin et al. |
| 2005/0263919 | A1 | 12/2005 | Lin et al. |
| 2005/0263920 | A1 | 12/2005 | Lin et al. |
| 2005/0263922 | A1 | 12/2005 | Lin et al. |
| 2005/0263927 | A1 | 12/2005 | Lin et al. |
| 2005/0263928 | A1 | 12/2005 | Lin et al. |
| 2005/0263929 | A1 | 12/2005 | Lin et al. |
| 2005/0263930 | A1 | 12/2005 | Lin et al. |
| 2005/0263931 | A1 | 12/2005 | Lin et al. |
| 2005/0267587 | A1 | 12/2005 | Lin et al. |
| 2005/0267588 | A1 | 12/2005 | Lin et al. |
| 2005/0267589 | A1 | 12/2005 | Lin et al. |
| 2005/0267592 | A1 | 12/2005 | Lin et al. |
| 2005/0267593 | A1 | 12/2005 | Lin et al. |
| 2005/0267604 | A1 | 12/2005 | Lin et al. |

FOREIGN PATENT DOCUMENTS

| | | |
|---|---|---|
| JP | 06-228011 | 8/1994 |
| WO | WO 03/055418 | 7/2003 |

OTHER PUBLICATIONS

PCT/US04/11637 International Search Report/Written Opinion, mailed Mar. 11, 2005, Examiner Boehm.

Sugawara et al., "Calcium Phosphate Cement: An In Vitro Study of Dentin Hypersensitivity Using Calcium Phosphate Cement", The Journal of the Japanese Society for Dental Materials and Devices, 1989, vol. 8, pp. 282-294.

Pickel et al., "The Effects of a Chewing Gum Containing Dicalcium Phosphate on Salivary Calcium and Phosphate", Ala. J. Med. Sci., 1965, vol. 2, pp. 286-287.

Matsuya et al., "Effects of pH on the Reactions of Tetracalcium Phosphate and Dicalcium Phosphate", IADR Abstract, Apr. 1991.

Sugawara et al., "Formation of Hydroxyapatite in Hydrogels from Tetracalcium Phosphate/Dicalcium Phosphate Mixtures," J. Nihon. Univ. Sch. Dent., 1989, vol. 31, pp. 372-381.

Hong et al., "The Periapical Tissue Reactions to a Calcium Phosphate Cement in the Teeth of Monkeys," J. Biomed. Mater. Res., Apr. 1991, vol. 25(4), pp. 485-498.

de Rijk, et al., "Clinical Evaluation of a Hydroxyapatite Precipitate for the Treatment of Dentinal Hypersensitivity," Biomedical Engineering v. Recent Developments, Proc. of 5th Southern Biomedical Engineering Conference, 1986, pp. 336-339. (Pergamon Press, New York).

Gruninger et al., "Evaluation of the Biocompatability of a New Calcium Phosphate Setting Cement," J. Dent. Res., 1984, 63, Abst. No. 270 (4 pages).

Costantino et al., "Evaluation of a New Hydroxyapatite Cement: Part III: Cranioplasty in a Cat Model," The Fifth Intl. Symposium on Facial Plastic Reconstructive Surgery of the Head and Neck, Toronto, Canada, 1989. (18 pages).

Shindo, et al., "Facial Skeletal Augmentation Using Hydroxyapatite Cement," Arch. Otolaryngol. Head Neck Surg., 1993, vol. 119, pp. 185-190.

Briner et al., "Significance of Enamel Remineralization", J. Dent. Res., 1974, vol. 53, pp. 239-243.

Silverstone L.M., "Remineralization Phenomena", Caries Res. 1977, vol. 11 (Supp. 1), pp. 59-84.

Costantino et al., "Hydroxyapatite Cement: I. Basic Chemistry and Histologic Properties," Arch. Otolaryngol. Head Neck Surg., 1991, vol. 117, pp. 379-394.

Friedman et al., "Hydroxyapatite Cement: II. Obliteration and Reconstruction of the Cat Frontal Sinus," Arch. Otolary. Head Neck Surg., 1991, vol. 117, pp. 385-389.

Costantino et al., "Experimental Hydroxyapatite Cement Cranioplasty," Plast. Reconstr. Surg., 1992, vol. 90, No. 2, pp. 174-185.

Miyazaki et al., "An Infrared Spectroscopic Study of Cement Formation of Polymeric Calcium Phosphate Cement," The Journal of the Japanese Society for Dental Materials and Devices, 1992, vol. 11, No. 2, pp. 278-284.

Driskell et al., "Development of Ceramic and Ceramic Composite Devices for Maxillofacial Applications", J. Biomed. Mater. Res. Symposium, 1972, vol. 6, No. 2 (part 2), pp. 345-361.

Hiatt et al., "Root Preparation I. Obturation of Dentinal Tubules in Treatment of Root Hypersensitivity", J. Periodontol., 1972, vol. 41, No. 6, pp. 373-380.

Patel et al., "Solubility of $CaHPO_4$ $2H_2O$ in the Quaternary System $Ca(OH)_2$-$H_3PO_4$-NaCl-$H_2O$ at 25° C., " J. Res. Nat. Bur. Stand. (Physics Chem.), 1974, vol. 78A, pp. 675-681.

Salyer et al., "Porous Hydroxyapatite as an Onlay Bone-Graft Substitute for Maxillofacial Surgery," Presented at the 54th Annual Scientific Meeting of the American Society of Plastic and Reconstructive Surgeons, Kansas City, Missouri, 1985, pp. 236-244.

Kenney et al., "The Use of a Porous Hydroxylapatite Implant in Periodontal Defects: II. Treatment of Class II Furcation Lesions in Lower Molars," J. Periodontol, 1988, pp. 67-72.

Zide et al., "Hydroxylapatite Cranioplasty Directly Over Dura," J. Oral Maxillofac. Surg., 1987, vol. 45, pp. 481-486.

Waite et al., "Zygomatic Augmentation with Hydroxylapatite: A Preliminary Report," J. Oral Maxillofac. Surg., 1986, pp. 349-352.

Verwoerd, et al. Porous Hydroxylapatite-perichondrium Graft in Cricoid Reconstruction, Acta Otolaryngol., 1987, vol. 103, pp. 496-502.

Grote, "Tympanoplasty With Calcium Phosphate," Arch. Otolaryngol., 1984, vol. 110, pp. 197-199.

Kent et al., "Alveolar Ridge Augmentation Using Nonresorbable Hydroxylapatite with or without Autogenous Cancellous Bone," J. Oral Maxillofac. Surg., 1983, vol. 41, pp. 629-642.

Piecuch, J.F., "Augmentation of the Atrophic Edentulous Ridge with Porous Replamineform Hydroxyapatite (Interpore-200)", Dental Clinics of North America, 1986, vol. 30(2), pp. 291-305.

Misch, C.E., "Maxillary Sinus Augmentation for Endosteal Implants: Organized Alternative Treatment Plans," Int. J. Oral. Implant., 1987, vol. 4(2), pp. 49-58.

Chohayeb, et al., "Evaluation of Calcium Phosphate as a Root Canal Sealer-Filler Material," J. Endod., 1987, vol. 13, pp. 384-386.

Brown et al., "Crystallography of Tetracalcium Phosphate," J. Res. Nat. Bur. Stand. (Physics Chem.), 1965, vol. 69A, pp. 547-551.

Sanin et al., "Particle Size Effects on pH and Strength of Calcium Phosphate Cement," IADR Abstract, Apr. 1991.

Chow et al., "X-ray Diffraction and Electron Microscopic Characterization of Calcium Phosphate Cement Setting Reactions," IADR Abstract, 1987.

Block et al. "Correction of Verticle Orbital Dystopia with a Hydroxylapatite Orbital Floor Graft," J. Oral Maxillofac. Surg., 1988, vol. 46, pp. 420-425.

Brown, W.E., "Solubilities of Phosphates and Other Sparingly Soluble Compounds", Environmental Phosphorous Handbook, 1973, pp. 203-239. (John Wiley & Sons, New York).

Gregory et al., "Solubility of $CaHPO_4$ $2H_2O$ in the System $Ca(OH)_2$-$H_3PO_4$-$H_2O$ at 5, 15, 25, and 37.5° C.," J. Res. Nat. Bur. Stand. (Physics Chem.), 1970, vol. 74A, No. 4, pp. 461-475.

Gregory et al., "Solubility of $\beta$-$Ca_3(PO_4)_2$ in the System $Ca(OH)_2$-$H_3PO_4$-$H_2O$ at 5, 15, 25 and 37° C.," J. Res. Nat. Bur. Stand. (Physics Chem.), 1974, vol. 78A, No. 6, pp. 667-674.

McDowell et al., "Solubility of $Ca_5(PO_4)_3OH$ in the System $Ca(OH)_2$-$H_3PO_4$-$H_2O$ at 5, 15, 25 and 37° C.," J. Res. Nat. Bur. Stand. (Physics Chem.), 1977, vol. 91A, Nos. 2 and 3, pp. 273-281.

McDowell et al., "Solubility Study of Calcium Hydrogen Phosphate. Ion Pair Formation," Inorg. Chem., 1971, vol. 10, pp. 1638-1643.

Moreno et al., "Stability of Dicalcium Phosphate Dihydrate in Aqueous Solutions and Solubility of Octocalcium Phosphate," Proc. Soil Sci. Soc. Am., 1960, vol. 21, pp. 99-102.

Chow et al, "Self-Setting Calcium Phosphate Cements," Mat. Res. Soc. Symp. Proc., vol. 179, 1991, pp. 3-23.

Miyazaki et al., "Chemical Change of Hardened PCA/CPC Cements in Various Storing Solutions", The Journal of the Japanese Society for Dental Materials and Devices, 1992, vol. 11, No. 2, pp. 324-330.

Fukase et al, "Thermal Conductivity of Calcium Phosphate Cement", IADR Abstract, Mar. 1990.

Sugawara et al., "Biocompatibility and Osteoconductivity of Calcium Phosphate Cement", IADR Abstract, Mar. 1990.

Miyazaki et al., "Polymeric Calcium Phosphate Cements", IADR Abstract, Mar. 1990.

Link et al., "Composite of Calcium Phosphate Cement and Genetically Engineered Protein Bioadhesive," IADR Abstract, Mar. 1991.

Chow, "Development of Self-Setting Calcium Phosphate Cements", Journal of The Ceramic Society of Japan, 1991, vol. 99 [10], pp. 954-964.

Brown et al., A New Calcium Phosphate, Water Setting Cement, Cements Research Progress 1986, P.W. Brown, Ed., Westerville, Ohio: American Ceramic Society, 1988, pp. 352-379.

Sugawara et al., "A Calcium Phosphate Root Canal Sealer-Filler" IADR Abstract, 1987.

Sugawara et al., "In Vitro Evaluation of the Sealing Ability of a Calcium Phosphate Cement When Used as a Root Canal Sealer-Filler," J. Endodon., 1990, vol. 16, No. 4, pp. 162-165.

Chow, L.C., "Calcium Phosphate Materials: Reactor Response," Adv. Dent. Res., 1988, vol. 2(1), pp. 181-184.

Fukase et al., "Setting Reactions and Compressive Strengths of Calcium Phosphate Cements", J. Dent. Res., 1990, vol. 69(12), pp. 1852-1856.

Miyazaki et al., "Cements," Guide to Dental Materials and Devices, 7th Edition, 1974-1975, Chapter 6.

Sugawara et al., "Formation of Hydroxyapatite in Hydrogels from Tetracalcium Phosphate/Dicalcium Phosphate Mixtures," J. Nihon Univ. Sch. Dent., vol. 31, 372-381, 1989.

Chow et al. "A Natural Bone Cement-A Laboratory Novelty Led to the Development of Revolutionary New Biomaterials", J. Res. Natl. Inst. Stand. Technol., 2001, vol. 106, pp. 1029-1033.

Gburek et al., "Mechanical Activation of Tetracalcium Phosphate," J. Am. Ceramics Soc., vol. 87(2), pp. 311-313.

* cited by examiner

METHOD FOR MAKING A POROUS CALCIUM PHOSPHATE ARTICLE

PRIORITY CLAIM

This application is a continuation of and claims the benefit of priority under 35 U.S.C. § 120 to co-pending U.S. patent application Ser. No. 10/780,728 entitled "METHOD FOR MAKING A POROUS CALCIUM PHOSPHATE ARTICLE" filed on Feb. 19, 2004, herein incorporated by reference.

BACKGROUND OF THE INVENTION

1. Field of the Invention

The present invention is related to a porous calcium phosphate article for use as a medical implant, and in particular to a method of making a porous calcium phosphate scaffold for use as tissue-engineered scaffold.

2. Description of the Related Art

A tissue-engineered scaffold (majority made from biodegradable polymers) has a very porous structure that allows living cells (usually taken from the patient being treated) to penetrate into the structure and be "seeded" in-vitro during a cell culture process. After a period of time (days or weeks) of cell culture, the cell-seeded scaffold is implanted into either an animal (e.g., rat) whose immune system has been removed, or into the patient himself (usually under the skin for easier later-on process). During this period of time (weeks to months) the cells quickly multiply from absorbing nutrients from the animal or the patient's body, and, at the same time, the scaffold itself is gradually dissolved or resorbed. When this process is substantially "mature", the implant (now a real bone) is removed from under the skin of the animal or the patient and re-implanted into the (wounded or diseased) site being treated. The following are some references describing some details about the background, requirements, applications, etc. of tissue-engineered scaffold: U.S. Pat. Nos. 6,139,578; 6,200,606; 5,306,303; and 6,132,463.

It is advantageous if a tissue-engineered scaffold is bioresorbable, sufficiently porous and supportive at the same time. The conventional high temperature (usually >1000° C.)-sintered porous hydroxyapatite (HA) block material does not possess sufficient micro/nano-sized porosity and is hardly bioresorbable. On the other hand, the conventional biodegradable polymer for scaffold application exhibits a relatively low strength and too high a dissolution rate.

SUMMARY OF THE INVENTION

A primary objective of the invention is to provide a porous calcium phosphate article or block for use as a tissue-engineered scaffold, which is free from the aforesaid drawbacks in the prior art, or as a functional implant other than the tissue-engineered scaffold.

This objective is accomplished by providing a novel method for making a porous calcium phosphate article, which involves a) preparing a shaped article from a paste comprising a calcium phosphate cement, a pore-forming powder and a setting liquid; and b) immersing said shaped article in an immersing liquid for a period of time so that said pore-forming powder is dissolved in the immersing liquid, creating pores in said shaped article.

Features and advantages of the present invention are as follows:

1. The porous calcium phosphate article made according to the present invention can transform into an apatite-dominated material shortly after immersion in physiological solution or after implantation.
2. The porous calcium phosphate block made according to the present invention exhibits a higher strength than most other bioactive or biodegradable porous blocks with a similar porosity level.
3. The calcium phosphate block made according to the present invention possesses a significant amount of micro- and nano-sized porosity, that improves bioresorbability thereof.

DETAILED DESCRIPTION OF THE INVENTION

The preferred embodiments of the present invention include (but not limited thereto):

1. A method for making a porous calcium phosphate article comprising:
   i) preparing a shaped article from a paste comprising a calcium phosphate cement, a pore-forming powder and a setting liquid;
   ii) ii) immersing said shaped article in an immersing liquid for a first period of time so that said pore-forming powder is dissolved in the immersing liquid, creating pores in said shaped article;
   iii) removing the resulting porous shaped article from said immersing liquid; and
   iv) immersing the porous shaped article from step iii) in an impregnating liquid for a second period of time so that a compressive strength of the resulting article removed from the impregnating liquid is increased compared to that of said porous shaped article without said impregnating treatment,
   v) wherein step iii) is omitted and a compressive strength of the resulting porous shaped article removed from the immersing liquid after the first and the second periods of time is increased compared to that of the resulting porous shaped article removed after the first period of time, when the immersing liquid and the impregnating liquid are the same.
2. The method according to item 1, wherein said pore-forming powder is selected from the group consisting of LiCl, KCl, NaCl, $MgCl_2$, $CaCl_2$, $NaIO_3$, $KINa_3$, $PO_4$, $K_3PO_4$, $Na_2CO_3$, amino acid-sodium salt, amino acid-potassium salt, glucose, polysaccharide, fatty acid-sodium salt, fatty acid-potassium salt, potassium bitartrate ($KHC_4H_4O_6$), potassium carbonate, potassium gluconate ($KC_6H_{11}O_7$), potassium-sodium tartrate ($KNaC_4H_4O_6 \cdot 4H_2O$), potassium sulfate ($K_2SO_4$), sodium sulfate, and sodium lactate.
3. The method according to item 1, wherein the immersing liquid is an acidic aqueous solution, a basic aqueous solution, a physiological solution, an organic solvent, or a substantially pure water.
3. The method according to item 3, wherein the immersing liquid comprises at least one of Ca and P sources.
5. The method according to item 3, wherein the immersing liquid is a Hanks' solution, a HCl aqueous solution or an aqueous solution of $(NH_4)_2HPO_4$.
6. The method according to item 3, wherein the immersing liquid and the impregnating liquid are the same.
7. The method according to item 4, wherein the immersing liquid and the impregnating liquid are the same.
8. The method according to item 5, wherein the immersing liquid and the impregnating liquid are the same.

9. The method according to item 1, wherein the immersing liquid and the impregnating liquid are different.

10. The method according to item 9, wherein the impregnating liquid is an acidic solution, a basic solution, a physiological solution, or a substantially pure water.

11. The method according to item 10, wherein the impregnating liquid comprises at least one of Ca and P sources.

12. The method according to item 10, wherein the impregnating liquid is a Hanks' solution, a HCl aqueous solution or an aqueous solution of $(NH_4)_2HPO_4$.

13. The method according to item 1, wherein the first period of time is longer than 10 minutes.

14. The method according to item 13, wherein the first period of time is longer than 1 day.

15. The method according to item 1, wherein the second period of time is longer than 10 minutes.

16. The method according to item 15, wherein the second period of time is longer than 1 day.

17. The method according to item 1, wherein the immersing in step ii) and iv) is carried out at room temperature or at a temperature between about 30 and 90° C.

18. The method according to item 1, wherein said preparing of step i) comprises the following steps:
   (a) preparing a first powder as said calcium phosphate cement comprising at least one Ca source and at least one P source, or at least one calcium phosphate source;
   (b) mixing said first powder and the pore-forming powder with said setting liquid to form said paste, wherein said first powder and said setting liquid undergo a hardening reaction;
   (c) molding said paste into an article in a mold of a desired shape and size before said hardening reaction is complete; and
   (d) removing said molded article from said mold.

19. The method according to item 18, wherein said calcium phosphate source in step (a) comprises one or more calcium phosphates selected from the group consisting of alpha-tricalcium phosphate (α-TCP), beta-tricalcium phosphate (β-TCP), tetracalcium phosphate (TTCP), monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), calcium dihydrogen phosphate, calcium dihydrogen phosphate hydrate, acid calcium pyrophosphate, anhydrous calcium hydrogen phosphate, calcium hydrogen phosphate hydrate, calcium pyrophosphate, calcium triphosphate, calcium phosphate tribasic, calcium polyphosphate, calcium metaphosphate, anhydrous tricalcium phosphate, tricalcium phosphate hydrate, and amorphous calcium phosphate.

20. The method according to item 19, wherein said calcium phosphate source in step (a) is tetracalcium phosphate (TTCP).

21. The method according to item 19, wherein the calcium phosphate source comprises at least one calcium phosphate particle having calcium phosphate whiskers on the surface of said calcium phosphate particle, wherein said calcium phosphate whiskers have a length of about 1–5000 nm and a width of about 1–500 nm.

22. The method according to item 19, wherein the setting liquid in step (b) is an acidic solution, a basic solution, or substantially pure water.

23. The method according to item 22, wherein said acidic solution is selected from the group consisting of nitric acid ($HNO_3$), hydrochloric acid (HCl), phosphoric acid ($H_3PO_4$), carbonic acid ($H_2CO_3$), sodium dihydrogen phosphate ($NaH_2PO_4$), sodium dihydrogen phosphate monohydrate ($NaH_2PO_4.H_2O$), sodium dihydrogen phosphate dihydrate, sodium dihydrogen phosphate dehydrate, potassium dihydrogen phosphate ($KH_2PO_4$), ammonium dihydrogen.phosphate ($NH_4H_2PO_4$), malic acid, acetic acid, lactic acid, citric acid, malonic acid, succinic acid, glutaric acid, tartaric acid, oxalic acid and their mixture.

24. The method according to item 22, wherein said basic solution is selected from the group consisting of ammonia, ammonium hydroxide, alkali metal hydroxide, alkali earth hydroxide, disodium hydrogen phosphate ($Na_2HPO_4$), disodium hydrogen phosphate dodecahydrate, disodium hydrogen phosphate heptahydrate, sodium phosphate dodecahydrate ($Na_3PO_4.12H_2O$), dipotassium hydrogen phosphate ($K_2HPO_4$), potassium hydrogen phosphate trihydrate ($K_2HPO_4.3H_2O$), potassium phosphate tribasic ($K_3PO_4$), diammonium hydrogen phosphate (($NH_4)_2HPO_4$), ammonium phosphate trihydrate (($NH_4)_3PO_4.3H_2O$), sodium hydrogen carbonate ($NaHCO_3$), sodium carbonate $Na_2CO_3$, and their mixture.

25. The method according to item 18, wherein step (c) further comprises removing a portion of liquid from said paste, so that a liquid/powder ratio of said paste decreases.

26. The method according to item 18, wherein step (c) further comprises pressurizing said paste in said mold before said hardening reaction is complete to remove a portion of liquid from said paste, so that a liquid/powder ratio of said paste decreases.

27. The method according to item 26, wherein said pressuring is about 1 to 500 MPa.

28. The method according to item 26, wherein step (c) further comprises heating said paste during said pressurizing.

29. The method according to item 18, wherein step (c) further comprises heating said paste during molding.

30. The method according to item 1 further comprising removing the resulting porous shaped article having an increased compressive strength from said impregnating liquid; and cleaning and drying said porous shaped article after removed from said impregnating liquid.

31. The method according to item 30 further comprising heating the resulting cleaned and dried porous shaped article.

32. The method according to item 31, wherein said heating is conducted at a temperature between 50 and 500° C.

33. The method according to item 1, wherein said paste in step i) further comprises living cells.

34. The method according to item 1, wherein said immersing liquid in step ii) comprises living cells.

35. The method according to item 1, wherein said impregnating liquid in step iv) comprises living cells.

36. The method according to item 1, wherein said porous shaped article having an increased compressive strength removed from said impregnating liquid in step iv) has a porosity of at least 30 vol %.

37. The method according to item 1, wherein said porous shaped article having an increased compressive strength removed from said impregnating liquid in step iv) has a porosity of 50–90 vol %.

The porous shaped calcium phosphate article made according to the method of the present invention may be used as a tissue-engineered scaffold, medical implant or a reinforcing constituent of a composite.

The following examples are intended to demonstrate the invention more fully without acting as a limitation upon its scope, since numerous modifications and variations will be apparent to those skilled in this art.

PREPARATIVE EXAMPLE 1

Preparation of TTCP Powder

A $Ca_4(PO_4)_2O$ (TTCP) powder was prepared by mixing $Ca_2P_2O_7$ powder with $CaCO_3$ powder uniformly in ethanol for 24 hours followed by heating to dry. The mixing ratio of $Ca_2P_2O_7$ powder to $CaCO_3$ powder was 1:1.27 (weight ratio) and the powder mixture was heated to 1400° C. to allow two powders to react to form TTCP.

PREPARATIVE EXAMPLE 2

Preparation of Non-dispersive TTCP/DCPA-based CPC Powder (Abbreviated as ND-CPC)

The TTCP powder prepared according to the method of PREPARATIVE EXAMPLE 1 was sieved and blended with dried $CaHPO_4$ (DCPA) powder in a ball mill for 12 hours. The blending ratio of the TTCP powder to the DCPA powder was 1:1 (molar ratio). The resultant powder mixture was added to a 25 mM diluted solution of phosphate to obtain a powder/solution mixture having a concentration of 3 g powder mixture per 1 ml solution while stirring. The resulting powder/solution mixture was formed into pellets, and the pellets were heated in an oven at 50° C. for 10 minutes. The pellets were then uniformly ground in a mechanical mill for 20 minutes to obtain the non-dispersive TTCP/DCPA-based CPC powder (ND-CPC). The particles of this ND-CPC powder have whiskers on the surfaces thereof.

EXAMPLE 1

Effect of KCl Content and Immersion Time on Compressive Strength of Porous CPC Block To a setting solution of 1M phosphoric acid solution (pH=5.89) the ND-CPC powder from PREPARATIVE EXAMPLE 2 was added in a liquid/powder ratio (L/P ratio) of 0.4, i.e. 4 ml liquid/10 g powder, while stirring. KCl powder in a predetermined amount was mixed to the resulting mixture by stirring intensively. The resulting paste was filled into a cylindrical steel mold having a length of 12 mm and a diameter of 6 mm, and was compressed with a gradually increased pressure until a maximum pressure of 3.5 MPa was reached. The maximum pressure was maintained for one minute, and then the compressed CPC block was removed from the mold. At the 15$^{th}$ minute following the mixing of the liquid and powders, the compressed CPC block was immersed in a deionized water at 37° C. for 4 day, 8 days, and 16 days. The compressive strength of the specimens of the three different periods of immersion time was measured by using a AGS-500D mechanical tester (Shimadzu Co., Ltd., Kyoto, Japan) after the specimens were dry. The measured dry specimen compressive strength is listed Table 1.

TABLE 1

| KCl/CPC ratio by weight | Dry compressive strength (MPa) Immersion time (Day) | | |
| --- | --- | --- | --- |
|  | 4 day | 8 days | 16 days |
| 1 | 7.0 | 5.4 | 6.6 |
| 1.5 | 3.9 | 2.7 | 4.3 |
| 2 | 1.3 | 2.3 | 2.6 |

It can seen from Table 1 that the dry compressive strength of the porous CPC blocks decreases as the KCl/CPC ratio by weight increases.

EXAMPLE 2

Effect of KCl Content on Compressive Strength and Porosity of Porous CPC Block The procedures of EXAMPLE 1 were repeated except that the immersion time was set at four days, and more KCl/CPC ratios by weight were chosen. The results are listed in Table 2.

TABLE 2

| KCl/CPC ratio by weight | Dry compressive strength (MPa) | Porosity (vol %)* |
| --- | --- | --- |
| 1 | 8.0 | 66.8 |
| 1.25 | 5.0 | 69.7 |
| 1.5 | 3.9 | 72.2 |
| 1.75 | 2.9 | 74.4 |
| 2 | 1.3 | 76.5 |
| 3 | 0.4 | 81.9 |

*Porosity (vol %) was measured by Archimedes' method, and calculated as in ASTM C830.

The results in Table 2 show that the porosity of the porous CPC block becomes greater as the KCl/CPC ratio by weight increases. Morphology of the porous CPC blocks prepared in this example with the KCl/CPC ratios by weight of 1.25, 1.5, 1.75 and 2.0 shows macro and micro-pores, which were observed with SEM.

EXAMPLE 3

Effect of KCl Content and Heat Treatment on Dry Compressive Strength of Porous CPC Block The procedures of EXAMPLE 1 were repeated except that the immersing time was set at 4 days and the resulting porous CPC block was heat treated. The heat treatment included placing the porous CPC block in an oven at 50° C. for 1 day; and then heating the dried porous CPC block in a furnace at the temperature and for a period of time set in Table 3 with a heating rate of 10° C./min. The compressive strength was measured after cooling of the heated CPC block. The conditions and results are listed in Table 3.

TABLE 3

| KCl/CPC ratio by weight | Heat treatment conditions | Dry compressive strength (MPa) |
| --- | --- | --- |
| 1 | No | 7 |
|  | 350° C., 1 hr | 8.5 |
|  | 350° C., 2 hrs | 9.6 |
| 1.5 | No | 3.9 |
|  | 400° C., 2 hr | 4.6 |

The data in Table 3 show that the heat treatment can enhance the dry compressive strength of the porous CPC block.

EXAMPLE 4

Effect of Molding Pressure and Immersing Liquid on Dry Compressive Strength of Porous CPC Block The procedures of EXAMPLE 1 were repeated except that the maximum pressure used to compress the paste in the mold was changed from 3.5 MPa to the values listed in Table 4 and the immersion conditions were also changed as indicated in Table 4. Further, the KCl/CPC ratio by weight was set at 2. The conditions and results are listed in Table 4.

TABLE 4

| Mold pressure | Immersion conditions | Dry compressive strength (MPa) |
|---|---|---|
| 3.5 MPa | 37° C. Deionized water, 4 days | 1.3 |
| 50 MPa | 37° C. Deionized water, 4 days | 4.7 |
| 156 MPa | 37° C. Hanks' solution, 1 day; 37° C. deionized water, 3 days | 5 |
| 156 MPa | 37° C. Deionized water, 1 day; 37° C. Hanks' solution 3 days | 4.2 |
| 156 MPa | 37° C. Hanks' solution, 8 days | 6 |
| 167 MPa | 90° C. deionized water, 5 hrs | 2.7 |
| 167 MPa | 90° C. deionized water, 5 hrs; Hank.s solution 4 days | 3.7 |

The data in Table 4 reveal that the dry compressive strength of the porous CPC block increases as the pressure used to compress the paste in the mold increases.

EXAMPLE 5

Porosity and Compressive Strength of Porous CPC Blocks Prepared from Different Pore-forming Powders The procedures of EXAMPLE 1 were repeated by using sugar, KI, $C_{17}H_{33}COONa$ and $C_{13}H_{27}COOH$ instead of KCl. The immersion time was 14 days in deionized water. In the cases where the $C_{17}H_{33}COONa$ and $C_{13}H_{27}COOH$ were used, the CPC blocks were further immersed in ethanol for additional four days. The conditions and the results are listed in Table 4.

TABLE 5

| Pore-forming powder | S[a] | C.S. (MPa)[b] | Porosity (vol %)[c] |
|---|---|---|---|
| Sugar | 1 | 4.1 | 58.4 |
| KI | 2 | 4.3 | 62.2 |
| KI | 3 | 1.7 | 75.5 |
| C17H33COONa | 1 | 8.0 | 56.0 |
| C13H27COOH | 2 | 5.9 | 60.1 |

[a] S = Pore-forming powder/CPC by volume.
[b] C.S. = dry compressive strength (hereinafter abbreviated as C.S.).
[c] Porosity: defined as in Table 2 (hereinafter the same definition will be used unless otherwise indicated).

It can be seen from Table 5 that various powders which are soluble in water can be used in the preparation of a porous CPC block according to the method of the present invention.

EXAMPLE 6

Effect of Immersion Solution and Immersion Temperature on C.S. and Porosity

In this example various immersing liquids at different temperatures were used to prepare porous CPC blocks by repeating the procedures in EXAMPLE 1, wherein the immersion time was set at 14 days, KI was used to replace KCl, and KI/CPC ratio by volume was set at 3. The conditions and results are listed in Table 6.

TABLE 6

| immersion solution | Immersion temperature (° C.) | C.S. | Porosity % |
|---|---|---|---|
| deionized water | 37 | 1.76 | 75.5 |
| deionized water | 25 | 2.2 | — |
| Ca(OH)$_2$ (0.03 M) | 37 | 2.06 | 74.7 |
| NaOH (0.03 M) | 37 | 2.14 | 75.1 |
| CaCl$_2$ (0.03 M) | 37 | 2.03 | 75.2 |
| NaOH (0.03 M) | 25 | 2.54 | 73.1 |

It can been seen from Table 6 that various aqueous solutions which are able to dissolve the pore-forming powder can be used in the preparation of a porous CPC block according to the method of the present invention.

EXAMPLE 7

Effect of Heat Treatment on C.S. and Porosity

The procedures of EXAMPLE 1 were repeated except that the immersion time was set at 14 days, KI was used to replace KCl, and KI/CPC ratio by volume was set at 3. Further the porous CPC block removed from the immersing liquid (deionized water at 37° C.) was dried in an oven and then subjected to a heat treatment at 100–800° C. for a period of 2–10 hours in high temperature furnace with a heating rate of 10° C./min. The conditions and results are listed in Table 7.

TABLE 7

| Heat treatment condition | C.S. (MPa) |
|---|---|
| No | 1.7 |
| 100° C. - 2 hr | 1.7 |
| 200° C. - 2 hr | 2.4 |
| 400° C. - 2 hr | 2.7 |
| 600° C. - 2 hr | 1.5 |
| 800° C. - 2 hr | 1.4 |
| 400° C. - 10 hr | 2.2 |
| 800° C. - 10 hr | 1.4 |

As shown in Table 7 the optimal conditions for the heat treatment is 400° C. for two hours, thereby the dry compressive strength of the porous CPC block was increased from 1.7 to 2.7 MPa.

EXAMPLE 8

Effect of NaCl Content and Immersion Temperature on C.S. and Porosity

The procedures of EXAMPLE 1 were repeated except that NaCl was used to replace KCl, and NaCl/CPC ratio by weight was set in Table 8. Further the paste was immersed in the immersing liquid (deionized water at 37° C. and 60° C.) for 7 days. The conditions and results are listed in Table 8.

TABLE 8

| NaCl/CPC ratio | Dry compressive strength (MPa) Immersion temperatue (° C.) | |
| --- | --- | --- |
| by weight | 37 | 60 |
| 0 | 75.5 | 58.2 |
| 0.25 | 28.8 | 27.9 |
| 0.5 | 11.2 | 10.4 |
| 0.75 | 5.8 | 8.3 |
| 1 | 6.7 | 6.1 |
| 1.25 | — | 5.2 |

| NaCl/CPC ratio | Porosity (%) Immersion temperatue (° C.) | |
| --- | --- | --- |
| by weight | 37 | 60 |
| 0 | 33.3 | 37.3 |
| 0.25 | 46.1 | 41.9 |
| 0.5 | 49.4 | 54.3 |
| 0.75 | 56.1 | 59.4 |
| 1 | — | 64.2 |
| 1.25 | 63.9 | 67.9 |

EXAMPLE 9

Effect of NaCl Content and Heat Treatment on C.S.

The procedures of EXAMPLE 1 were repeated except that NaCl was used to replace KCl, the paste was immersed in the immersing liquid (deionized water at 37° C.) for 7 days, and NaCl/CPC ratio by weight was set in Table 9. Further. The resulting porous CPC block was heat treated. The heat treatment included heating the porous CPC block in a furnance at the temperature set in Table 9 for 1 hr with a heating rate of 10° C./min. The compressive strength was measured after cooling of the heated CPC block. The conditions and results are listed in Table 9.

TABLE 9

| Heat treatment | Dry compressive strength (MPa) NaCl/CPC ratio by weight | |
| --- | --- | --- |
| temperatue (° C.) | 0.25 | 0.5 |
| Without heat treatment | 28.8 | 11.2 |
| 50 | 38.8 | 16.1 |
| 100 | 36.8 | 21.0 |
| 200 | 46.1 | 29.5 |
| 350 | 54.5 | 30.0 |
| 400 | 39.4 | 29.5 |
| 450 | 36.6 | 18.3 |

In the other preferred embodiments of the present invention $Na_2CO_3$ was used as the pore-forming powder in the preparation of the porous CPC blocks, which had the dry compressive strength and the porosity comparable to those disclosed in Examples 1–9.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A method of forming a porous calcium phosphate article comprising: adding a paste to a mold, wherein the paste comprises at least one calcium phosphate compound combined with at least one pore forming powder and at least one setting liquid; removing at least a portion of the setting liquid from the paste by subjecting the paste to a molding pressure of greater than 1 MPa to form a hardened calcium phosphate article; and immersing the hardened calcium phosphate article in one or more immersing liquids to form the porous calcium phosphate article.

2. The method of claim 1, further comprising applying heat to the paste before or while the molding pressure is applied to the paste.

3. The method of claim 1, further comprising heating the porous calcium phosphate article to between about 100° C. to about 800° C.

4. The method of claim 1, wherein the calcium phosphate compound is selected from the group consisting of alpha-tricalcium phosphate ($\alpha$-TCP), beta-tricalcium phosphate ($\beta$-TCP), tetracalcium phosphate (TTCP), monocalcium phosphate monohydrate (MCPM), monocalcium phosphate anhydrous (MCPA), dicalcium phosphate dihydrate (DCPD), dicalcium phosphate anhydrous (DCPA), octacalcium phosphate (OCP), calcium dihydrogen phosphate, calcium dihydrogen phosphate hydrate, acid calcium pyrophosphate, anhydrous calcium hydrogen phosphate, calcium hydrogen phosphate hydrate, calcium pyrophosphate, calcium triphosphate, calcium phosphate tribasic, calcium polyphosphate, calcium metaphosphate, anhydrous tricalcium phosphate, tricalcium phosphate hydrate, and amorphous calcium phosphate.

5. The method of claim 1, wherein the calcium phosphate compound comprises at least one calcium phosphate particulate compound having calcium phosphate whiskers on the surface of the particles, wherein said calcium phosphate whiskers have a length of about 1–5000 nm and a width of about 1–500 nm.

6. The method of claim 1, wherein the pore forming powder is at least partially water-soluble.

7. The method of claim 1, wherein the pore forming powder comprises an inorganic salt.

8. The method of claim 1, wherein the pore forming powder comprises an organic salt.

9. The method of claim 1, wherein the pore forming powder is selected from the list consisting of LiCl, KCl, NaCl, $MgCl_2$, $CaCl_2$, $NaIO_3$, KI, $Na_3PO_4$, $K_3PO_4$, $Na_2CO_3$, amino acid-sodium salt, amino acid-potassium salt, glucose, polysaccharide, fatty acid-sodium salt, fatty acid-potassium salt, potassium bitartrate ($KHC_4H_4O_6$), potassium carbonate, potassium gluconate ($KC_6H_{11}O_7$), potassium-sodium tartrate ($KNaC_4H_4O_6 \cdot 4H_2O$), potassium sulfate ($K_2SO_4$), sodium sulfate, and sodium lactate.

10. The method of claim 1, wherein the weight ratio of pore forming powder-to-calcium phosphate compound is from about to 0.25 to about 3.0.

11. The method of claim 1, wherein the setting liquid comprises an acidic solution, a basic solution, or substantially pure water.

12. The method of claim 11, wherein said acidic solution is selected from the group consisting of nitric acid ($HNO_3$), hydrochloric acid (HCl), phosphoric acid ($H_3PO_4$), carbonic acid ($H_2CO_3$), sodium dihydrogen phosphate ($NaH_2PO_4$), sodium dihydrogen phosphate monohydrate ($NaH_2PO_4 \cdot H_2O$), sodium dihydrogen phosphate dihydrate, sodium dihydrogen phosphate dehydrate, potassium dihydrogen phosphate ($KH_2PO_4$), ammonium dihydrogen phosphate ($NH_4H_2PO_4$), malic acid, acetic acid, lactic acid, citric acid, malonic acid, succinic acid, glutaric acid, tartaric acid, oxalic acid and mixtures thereof.

13. The method of claim 11, wherein said basic solution is selected from the group consisting of ammonia, ammonium hydroxide, alkali metal hydroxide, alkali earth hydroxide, disodium hydrogen phosphate ($Na_2HPO_4$), disodium hydrogen phosphate dodecahydrate, disodium hydrogen phosphate heptahydrate, sodium phosphate dodecahydrate ($Na_3PO_4 \cdot 12H_2O$), dipotassium hydrogen phosphate ($K_2HPO_4$), potassium hydrogen phosphate trihydrate ($K_2HPO_4 \cdot 3H_2O$), potassium phosphate tribasic ($K_3PO_4$), diammonium hydrogen phosphate (($NH_4)_2HPO_4$), ammonium phosphate trihydrate (($NH4)_3PO4 \cdot 3H_2O$), sodium hydrogen carbonate ($NaHCO_3$), sodium carbonate $Na_2CO_3$, and mixtures thereof.

14. The method of claim 1, wherein applying the molding pressure further comprises reducing the liquid-to-powder ratio of the paste.

15. The method of claim 1, wherein the article is adapted for use as a medical implant.

16. The method of claim 1, wherein the one or more immersing liquids comprise a basic solution, an acidic solution, a solution of substantially physiological pH, an organic solvent, or substantially pure water.

17. The method of claim 1, wherein at least one of the liquids comprises a solution of HCl, a solution of $(NH_4)_2HPO_4$, or Hank's solution.

18. The method of claim 1, wherein at least one of the liquids comprises at least one source of calcium and at least one source of phosphate.

19. The method of claim 1, wherein the hardened calcium phosphate article is immersed in one or more liquids for a period of time sufficient to remove at least a portion of the pore forming powder from the calcium phosphate article.

20. The method of claim 1, wherein the hardened calcium phosphate article is immersed in at least one liquid for at least 24 hours.

21. The method of claim 1, wherein the paste further comprises living cells.

22. The method of claim 1, wherein at least one of the liquids further comprises living cells.

* * * * *